United States Patent [19]
Naguib

[11] Patent Number: 6,114,177
[45] Date of Patent: Sep. 5, 2000

[54] FLUOROMETRIC ASSAY FOR MEASUREMENT OF ANTIOXIDANT ACTIVITY

[75] Inventor: Yousry Moustafa Aly Naguib, Burlington, Mass.

[73] Assignee: Phytochem Technologies, Inc., Chelmsford, Mass.

[21] Appl. No.: 08/967,952

[22] Filed: Nov. 12, 1997

[51] Int. Cl.$^7$ .................................................. G01N 21/64
[52] U.S. Cl. .............................. 436/172; 436/60; 436/71; 436/86
[58] Field of Search ................................ 436/172, 60, 71, 436/86

[56] References Cited

U.S. PATENT DOCUMENTS

| | | | |
|---|---|---|---|
| 4,269,938 | 5/1981 | Frank | 436/71 |
| 4,774,339 | 9/1988 | Haugland et al. | 548/405 |
| 5,338,854 | 8/1994 | Kang et al. | 548/110 |
| 5,372,936 | 12/1994 | Fraatz et al. | 436/172 |
| 5,395,755 | 3/1995 | Thorpe et al. | 436/172 |
| 5,460,943 | 10/1995 | Hayashi et al. | 436/172 |
| 5,554,502 | 9/1996 | Mithuhashi et al. | 436/172 |
| 5,605,809 | 2/1997 | Komoriya et al. | 436/86 |
| 5,614,386 | 3/1997 | Metzker et al. | 435/91 |
| 5,762,930 | 6/1998 | Fanger et al. | 424/136.1 |
| 5,804,395 | 9/1998 | Schade et al. | 435/7.4 |

FOREIGN PATENT DOCUMENTS

| | | | |
|---|---|---|---|
| 2252408 | 5/1992 | United Kingdom | 436/172 |

OTHER PUBLICATIONS

Holler, Tod. P.; Hpkins, Paul B. "A Qualitative Fluorescence–Based Assay for Tyrosyl Radical Scavenging Activity: Ovothiol A is an Efficient Scavenger." Analytical Biochemistry, 326–330, Aug. 1989.

Tsuchiya, M.; Scita, G.; Freisleben, H.; Kagan, V.; and Packer, L. "Antioxidant Radical–Scavenging Activity of Carotenoids and Retinoids Compared to alpha–Tocopherol." Methods in Enzymology, 460–472, 1992.

Karolin, J; Johansson, L.; Strandberg, L.; and Ny, T. "Fluorescence and Absorption Spectroscopic Properties of Dipyrrometheneboron Difluoride (BODIPY) Derivatives in Liquids, Lipid Membranes, and Proteins." J. Am. Chem. Soc., 7801–7806, Aug. 1994.

Park, D. K.; and Song, J. H. "Determination of the Antioxidant Activity of Vitamins C and E According to Lipid Physical State Using High Performance Liquid Chromatography with Chemiluminescence Detection." Korean Biochem. J., 473–478, 1994.

Makrigiorgos, G. M. "Detection of Lipid Peroxidation on Erythrocytes Using the Excimer–Forming Property of a Lipophilic BODIPY Fluorescent Dye." Biochem. and Biophys. Methods, 23–35, Aug. 1997.

Kang, M. Y.; Tsuchiya, M.; Packer, L.; and Manabe, M. "In Vitro study on Antioxidant Potential of Various Drugs Used in the Perioperative Period." Acta Anaesthesiologica Scand. 4–12, 1998.

*Primary Examiner*—Jill Warden
*Attorney, Agent, or Firm*—Hayes, Soloway, Hennessey, Grossman & Hage, PC

[57] ABSTRACT

A method for measuring total antioxidant activity of antioxidants utilizes BODIPY dyes which fluoresce in the visible region of the electromagnetic spectrum as a fluorescent reporter.

18 Claims, 8 Drawing Sheets

α-Tocopherol, R= (-CH$_2$CH$_2$CH$_2$CH)$_3$CH$_3$ with CH$_3$ branch  ; Trolox, R= (COOH)

BODIPY 581/591 C$_{11}$
( m = 2 , n = 10 )

Probucol

FLUOROMETRIC ASSAY FOR MEASUREMENT OF ANTIOXIDANT ACTIVITY

BRIEF DESCRIPTION OF INVENTION

1. Field of the Invention

The present invention relates to a new method to measure total antioxidant activity of antioxidants utilizing BODIPY dyes which fluoresce in the visible region of the electromagnetic spectrum as a fluorescent reporter.

2. Background and Prior Art

A well-established attribute of aerobic metabolism is the generation of reactive oxygen free radicals (ROS) by various enzymatic and non-enzymatic processes in living organisms. ROS play an important role in a variety of normal biological processes. Under certain unusual conditions, such as phagocytosis, exposure to radiation, ROS are excessively produced and cause oxidative damage to DNA, proteins, and lipids[1,2]. Cellular oxidative damage by free radicals has been implicated in the pathogenesis of various diseases and conditions including, congestive heart failure, cancer, rheumatoid arthritis, atherosclerosis, aging, diabetes, AIDS, inflammatory disorders, cataracts, and neuro-degenerative diseases such as Alzheimer's, Parkinson's, multiple sclerosis, and Down's syndrome[1-8].

Organisms have developed a variety of defenses, including enzymes and non-enzymatic antioxidants, to protect themselves from ROS. Antioxidants help cells to cope with oxidative stress by effectively quenching free radicals, and have been linked to diseases prevention[9]. Major antioxidants include proteins such as ferritin, transferritin and lactoferritin, and enzymes such as superoxide dismutase, catalase, and glutathione peroxidase. Major nonenzymatic antioxidants include maromolecules such as copper-binding ceruloplasmin, albumin, the iron-binding transferrin, hemoglobin; and small molecules which can be classified into water-soluble antioxidants (such as vitamin C, uric acid, bilirubin, reduced form of glutathione), and lipid-soluble antioxidants (such as vitamin E, carotenoids, retinoids, ubiquinol-10, phytochemicals). Fat soluble antioxidants are reported to play a major role as antioxidants in membranes and lipoproteins.[10-13]

Human serum and tissues contain many different antioxidants, and it would be relatively difficult to measure each antioxidant separately. It is both time consuming and expensive. In addition, since there seems to be cooperation between various antioxidants during oxidative stress, their combined action will be reflected in the total antioxidant activity[14]. Therefore, in order to assess the antioxidant status of individuals, for a possible therapeutic treatment with antioxidants, a simple method to measure total antioxidant activity is of great importance in the clinical field.

Because of the increasing interest in the natural antioxidants contained in dietary supplements, which are candidates for the prevention of oxidative damage caused by free radicals, pharmaceutical and nutraceutical companies claim and label their products to possess antioxidant activity. The Food and Drug Administration has issued new regulations requiring companies to substantiate their claims of antioxidant nutrients to be included on the label[15]. This also requires the development of a simple assay to measure antioxidants activity in food supplements, natural products and drugs.

Several direct and indirect methods for assaying antioxidant activity in vitro have been developed. The most commonly used method involves the inhibition of lipid peroxidation by antioxidants which are measured by the end-products, adducts or other indicators of oxidative damage (lipid hydroperoxides, thiobarbituric acid reactive products, malondialdehyde, conjugated dienes and others).[16,17]

Most of the other methods can be classified as chemiluminsecent, fluorometric and spectrophotometric assays. The chemiluminescent assay relies on the ability of antioxidants to quench light emission from a glowing oxidation reaction of a chemiluminescent substrate, such as luminol which emits at 420 nm.[18,19] The photometric methods include: (a) measurement of the change in the absorbance of the stable nitrogen free radical 1,1-diphenyl-2-picrylhydrazylradial (DPPH) in ethanol[20] and the stable radical cation ATBS$^+$ (prepared from 2,2'-azinobis(3-ethylbenzothiazoline-6-sulfonic acid) diammonium salt) in phosphate buffer[21-23] at 515 and 734 nm respectively, upon quenching by antioxidants; (b) the ability of antioxidants to inhibit autoxidation of linoleic acid in phosphate buffer,[24] (c) superoxide anion scavenging activity of antioxidants with xanthine/xanthine oxidase assay, as measured by the decrease in the absorbance of uric acid at 295 nm in buffer solution,[16] or by the reduction of the water-soluble nitro blue tetrazolium to brightly colored formazan.[24] The fluorometric methods are based on the loss of the fluorescence signal of the water-soluble fluorescent reporter molecule phycoerythrin in phosphate buffer,[25,26] and the lipid fluorescent reporter parinaric acid in hexane,[27,28] as a result of their interaction with peroxyl radicals, and the retention of the signal in the presence of antioxidants which intercept the free radicals. The chemiluminescent methods have some limitations, and the compounds to be tested should neither interact directly with the excited state of the chemiluminescent substrate nor absorb at the emission wavelength of the luminescent substrate.

The radicals 1,1-diphenyl-2-picrylhydrazyl (DPPH) and 2,2'-azinobis(3-ethylbenzothiazoline-6-sulfonic acid) diammonium salt (ATBS$^+$) are quite stable, and their properties differ from the highly reactive oxygen radicals, which are believed to play a major role in biological perioxidation processes. Except for the parinaric acid-based fluorescence assay, the above mentioned assays employ polar solvents, in which lipophilic antioxidants are either insoluble or sparingly soluble.

An important consideration in developing an assay is the sensitivity, reliability, and practicability. Fluorometry is a particularly important analytical technique due to its extreme sensitivity, which is orders of magnitude greater than that of spectrophotometric methods. The fluorometric assays reported in the literature are based on the use of either water-soluble phycoerythrin[29] or lipid-solution cis-parinaric acid[30] as fluorescent reporters, which lose their fluorescence upon oxidation by peroxyl radicals. Phycoerythrin absorbs in the visible range; however, it can only be employed in the aqueous medium. It has been reported that different lots of phycoerythrin behave differently in the oxygen radical absorbance capacity[31]. In addition, we found that phycoerythrin is both photochemically and thermally unstable. cis-Parinaric acid absorbs in the UV region where most of test samples (antioxidants) absorb, and also is very air sensitive and photolabile, undergoing photodimerization under illumination, resulting in loss of fluorescence.[32]

BRIEF DESCRIPTION OF THE INVENTION

To overcome these and other prior art problems, we developed a new and simple fluorometric assay based on the use of fluorescent reporters which belong to a class of dyes called BODIPY (4,4-difluoro-4-bora-3a, 4a-diaza-s-indacene) fluorophores, or so-called "BDY" dyes, in combination with a liopophilic peroxyl radical generator, in a non-polar solvent. These dyes absorb in visible light, and are both thermally and photochemically stable[32].

BRIEF DESCRIPTION OF THE DRAWINGS

Further understanding of the invention will be apparent from the following detailed description, taken in connection with the following drawings, wherein.

DETAILED DESCRIPTION OF PREFERRED EMBODIMENTS

Figure 1:
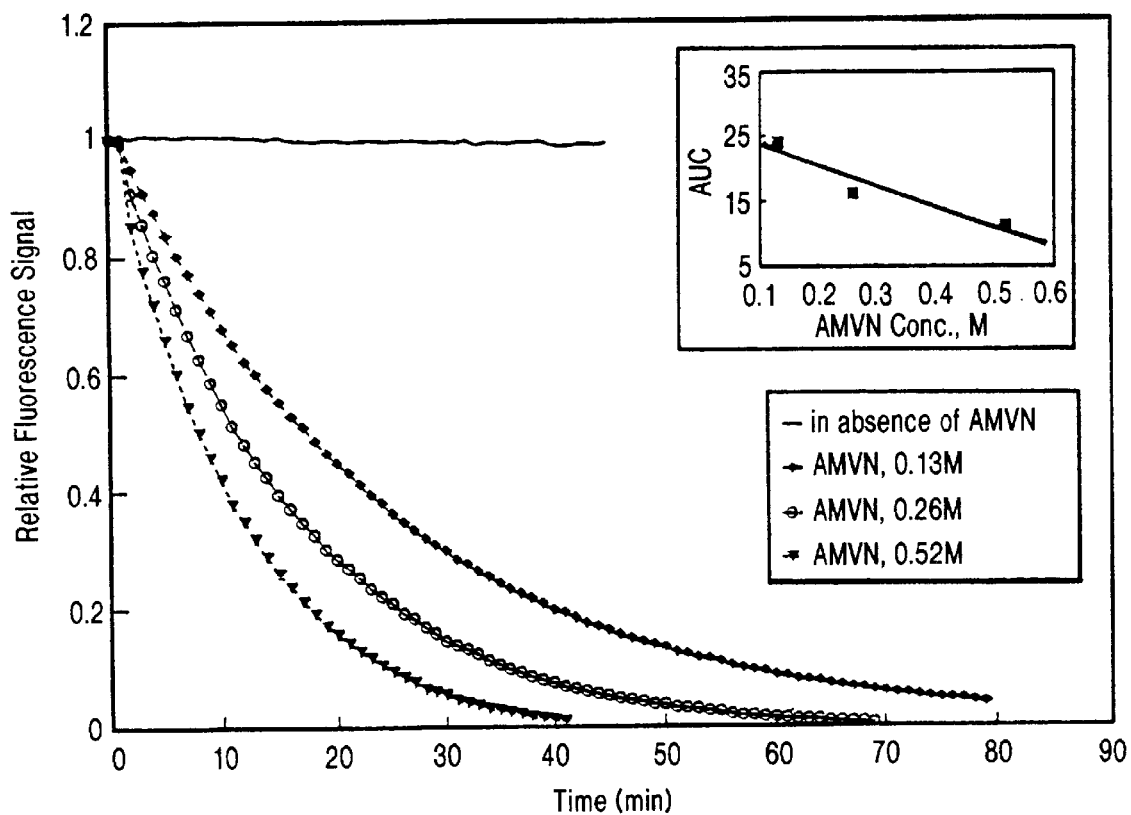
FIG. 1 shows time course of changes in BODIPY 581/591 $C_{11}$ fluorescence in octane butyronitrile (9:1) on incubation at 41° C. alone (—), or in the presence of different amounts of added 2,2'-azobis-2,4-dimethyl valeronitrile) (AMVN)

An assay for measurement of oxygen radical absorbance capacity (ORAC) requires three basic components: (a) a radical initiator (azo or peroxide-type) to generate oxygen radicals; (b) an indicator which upon oxidation by free radicals undergoes chemical and/or physical changes that can be analytically monitored; (c) a calibrator (standard) which interacts efficiently with peroxyl radicals.

As an indicator we chose BODIPY 581/591 $C_{11}$ (4,4-difluoro-5(4-phenyl-1,3-butadienyl)-4-bora-3a,4a-diaza-s-indacene-3-propionic acid), containing a long chain fatty acid, which makes it lipid soluble. BODIPY dyes are characterized by having a combination of non-polar structure, long wavelength absorption and fluorescence in the visible region, high extinction coefficient, high fluorescence quantum yield (0.9), and relatively high photostability[16]. The lipid-soluble azo compound 2,2'-azobis-2,4-dimethyl valeronitrile (AMVN) was chosen as a radical initiator since it thermally decomposes in air to generate a supply of peroxyl radicals[33]. 6-Hydroxy-2,5,7,8-tetramethyl-2-carboxylic acid (Trolox) was chosen as a standard antioxidant, because it is relatively stable compared to its analogue α-tocopherol (vitamin E). Octane containing a small amount of butyronitrile (10% v/v) was chosen as the solvent system to ensure the solubility of various components and to minimize the generation of solvent derived radicals, and to avoid loss of solvent by evaporation at the reaction temperature 41° C.

Fluorescence measurements were performed using a Shimadzu RF 1501 spectrofluorophotometer equipped with temperature controlled cell holder set at 41° C. All measurements were performed in a 1 cm quartz cuvette under stirring. The fluorescence signal of the indicator BODIPY 581/591 $C_{11}$ gradually decreases upon addition of peroxyl radical generating system AMVN. Peroxyl radicals are generated at a controlled rate by the thermal decomposition of AMVN in air. The indicator retains its fluorescence signal when exposed to AMVN in the presence of a peroxyl radial scavenger (antioxidant). Thus, the antioxidant potency of a substrate is directly measured by its ability to retain the fluorescence of BODIPY 581/591 $C_{11}$ in the presence of AMVN.

All fluorescence measurements are expressed relative to the initial reading, and are recorded every minute at the emission wavelength 600 nm, with excitation at 570 nm. The net protection area provided by an antioxidant sample is calculated using the difference between the area under curve of the BODIPY 581/591 $C_{11}$ fluorescence decay in the presence of an antioxidant sample ($AUC_{Sample}$) and in the absence of a sample (blank, $AUC_{Blank}$).

Trolox, an analogue of vitamin E is a highly efficient antioxidant and is used as a calibrator for antioxidant activity. Trolox has been found to partition 20–45% into the lipid phase of liposomes, and therefore it is expected to have some solubility in a non-polar organic solvent[34].

The Trolox equivalence of a sample on the basis of its weight relative to the weight of Trolox is given by:

Trolox equivalence per weight=$[(AUC_{Sample}-AUC_{Blank})/(AUC_{Trolex}-AUC_{Blank})]\cdot[(\text{weight of Trolox/weight of sample})]$ The Trolox equivalence of a sample on a molar basis is given by:

Trolox equivalence on molar basis=$[(AUC_{Sample}-AUC_{Blank})/(AUC_{Trolex}-ACU_{Blank})]\cdot[(\text{moles of Trolox/moles of sample})]$ where ($AUC_{Sample}-AUC_{Blank}$) and ($AUC_{Trolex}-AUC_{Blank}$) are the net protection areas under the curves of the BODIPY 581/591 $C_{11}$ fluorescence decay in the presence of a sample and Trolox, respectively. The area under curve (AUC) of the fluorescence decay of BODIPY 581/591 $C_{11}$ was calculated as described by Cao et al[25]. The advantage of using an area under curve of the net protection of the fluorescence of the indicator for evaluation of antioxidant activity in the peroxyl radical absorbance capacity assay has been previously discussed by Cao et al[25].

The final reaction mixture (3 ml) for the assay contained $1.3''\times10^{-9}$ M BODIPY 581/591 $C_{11}$, 0.26 M AMVN in octane/butyronitrile (9:1, v/v). As a standard, Trolox was assayed by adding 5 µl of a 0.16 M (267 µM in final concentration) Trolox stock solution in butyronitrile. Stock solutions of the samples were made in chloroform, of which 2 to 100 µl were added to the reaction mixture. Chloroform (100 µl) was shown to have no effect on the kinetic data of the blank (BODIPY 581/591 $C_{11}$/AMVN system).

Peroxyl Radical Oxidation of the Fatty Acid Indicator BODIPY 581/591 $C_{11}$

A solution of the fluorescent indicator BODIPY 581/591 $C_{11}$ in octane/butyronitrile (9:1, v/v) is both thermally and photochemically stable under the experimental condition (FIG. 1, curve a). Peroxyl radicals generated by thermolysis of AMVN oxidized BODIPY 581/591 $C_{11}$ to completion during 1 h incubation at 41° C. under air, as shown by the loss of the fluorescence signal of BODIPY 581/591 $C_{11}$ as monitored at 600 nm. The oxidation of BODIPY 581/591 $C_{11}$ was radical concentration dependent since without AMVN no loss of BODIPY 581/591 $C_{11}$ was observed (FIG. 1, curve a). In addition, as the concentration of added AMVN increases the rate of loss of BODIPY 581/591 $C_{11}$ increases (FIG. 1, curves b, c & d).

Peroxyl Radical Absorbency Capacity of Antioxidants

Figure 2:
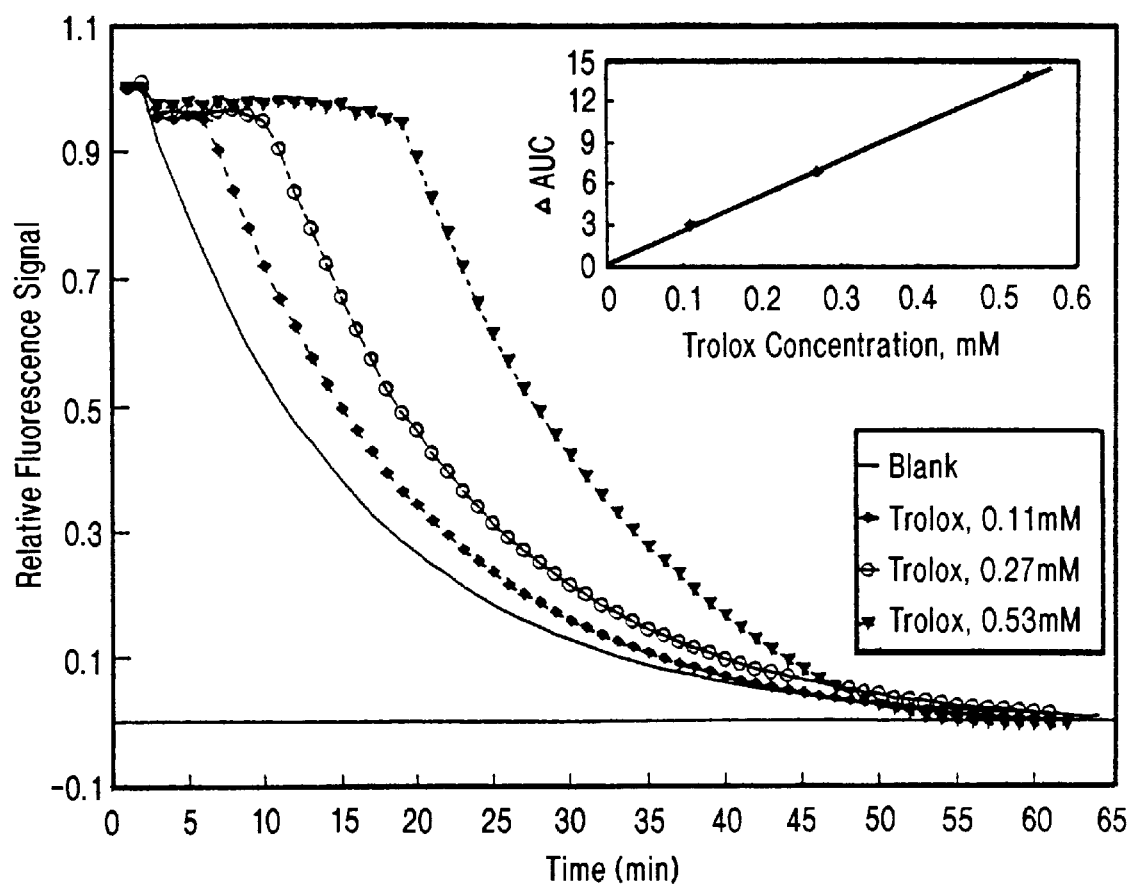
FIG. 2 shows time course of changes in BODIPY 581/591 $C_{11}$ fluorescence in octane/butyronitrile (9:1) on incubation at 41° C. with 0.26M AMVN, alone (—), or in the presence of varying amounts of 6-hydroxy-2,5,7,8-tetra-methyl chroman-2-carboxylic acid (Trolox)

Upon addition of Trolox and in the presence of AMVN, the rate of decrease in the fluorescence of BODIPY 581/591 $C_{11}$ showed a plateau region, after which the fluorescence decreased in a manner similar to that of the blank (FIG. 2). The initial plateau phase increases as the concentration of Trolox increases. The kinetic data obtained using different concentrations of Trolox is illustrated in FIG. 2. A linear correlation was found between ($AUC_{Trolox}-AUC_{Blank}$) values and the Trolox concentration. The average Trolox equivalence value found for different concentrations of Trolox is 1.07±0.07.

Figure 3:
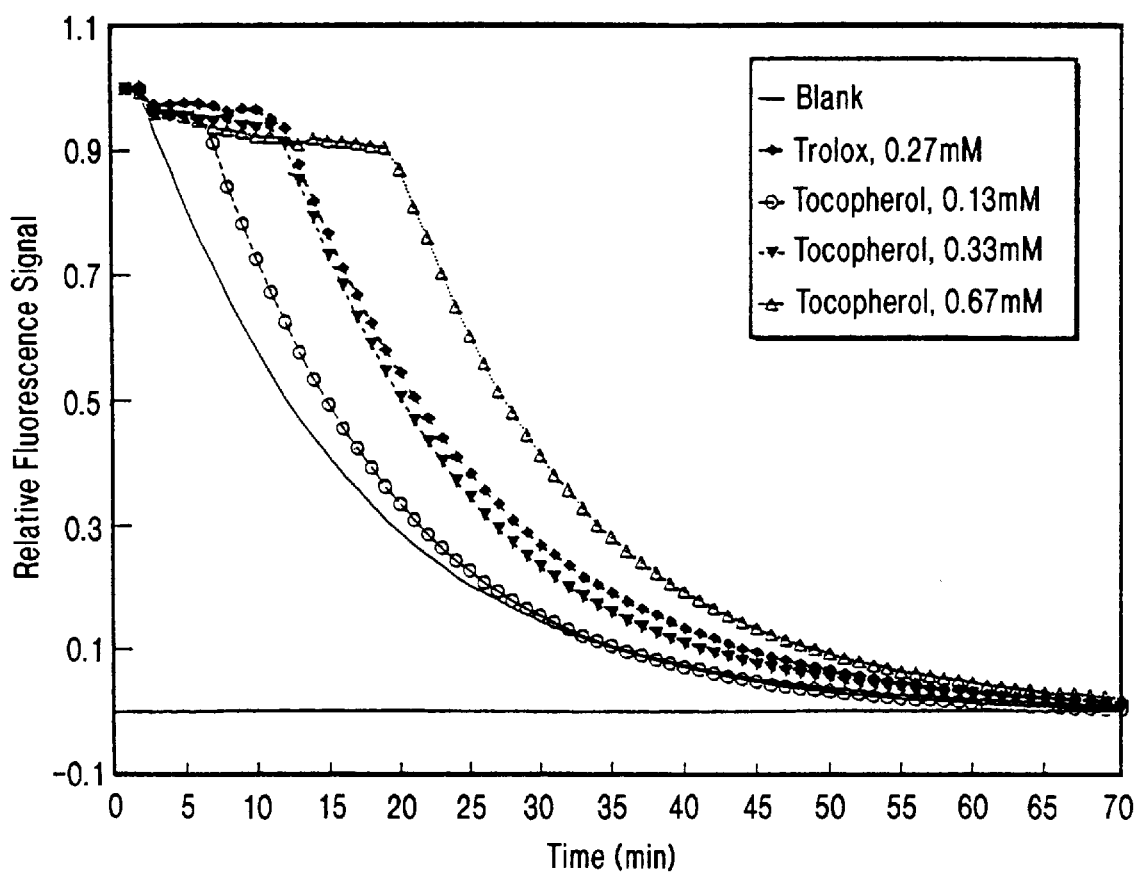
FIG. 3 shows time course of changes in BODIPY 581/591 $C_{11}$ fluorescence in octane/butyronitrile (9:1) on incubation at 41° C. with 0.26M AMVN, alone (—), or in the presence of 0.267 mM Trolox (♦—♦), or varying amounts of α-tocopherol.

A linear correlation was also found between ($AUC_{Sample}-AUC_{Blank}$) and α-tocopherol concentration. The average molar Trolox equivalence is 0.67±0.06. Again, the initial rate of fluorescence decay showed a plateau phase, the extent of which increased with higher concentrations of α-tocopherol (FIG. 3).

Figure 4:
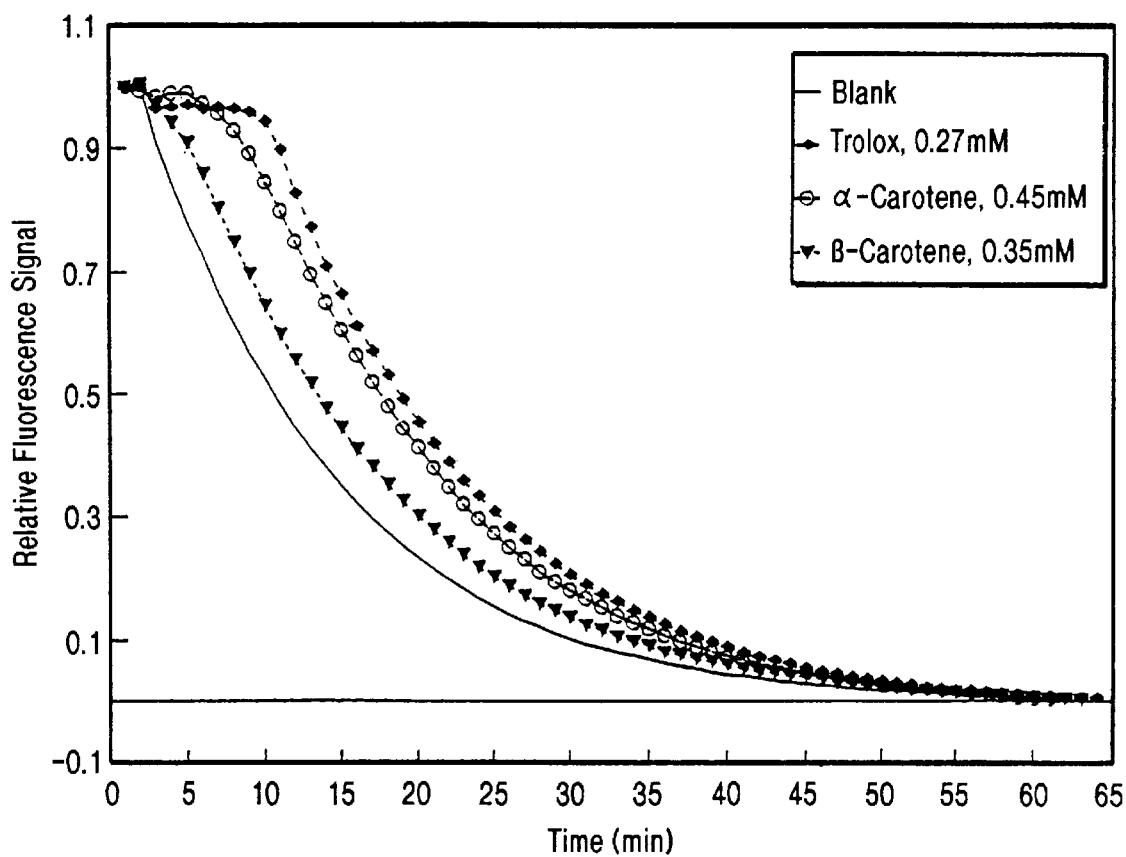
FIG. 4 shows time course of changes in BODIPY 581/591 $C_{11}$ fluorescence in octane/butyronitrile (9:1) on incubation at 41° C. with 0.26M AMVN, alone (—), or in the presence of 0.267 mM Trolox (♦—♦), or α-carotene, β-carotene; lutein.
Figure 5:
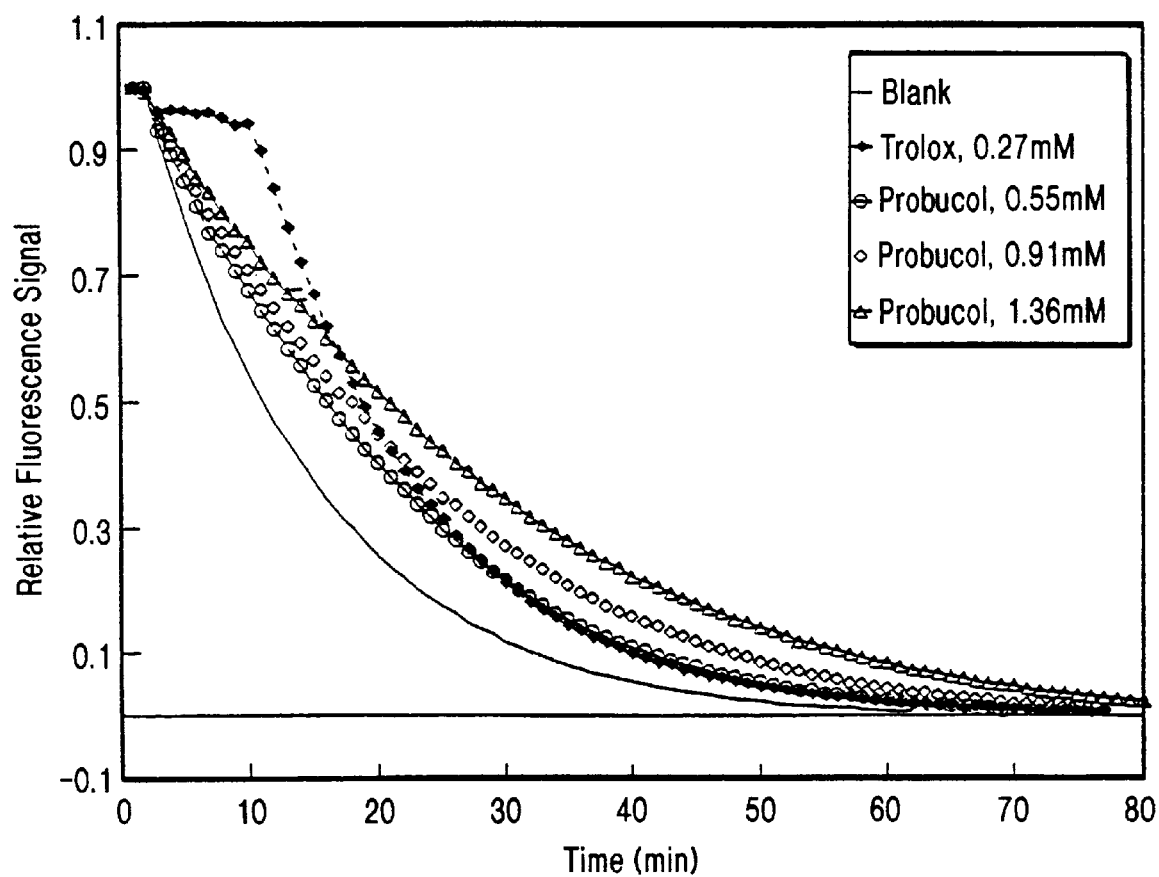
FIG. 5 shows time course of changes in BODIPY 581/591 $C_{11}$ fluorescence in octane/butyronitrile (9:1) on incubation at 41° C. with 0.26M AMVN, alone (—), or in the presence of 0.267 mM Trolox (♦—♦), or probucal.
Figure 6A:
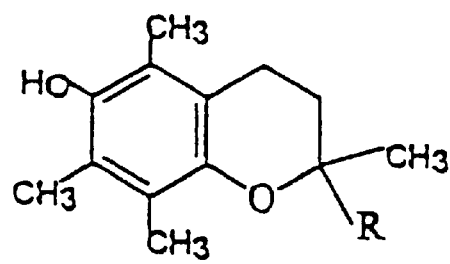
FIGS 6A–6C illustrate structural formulae.
Figure 6A:
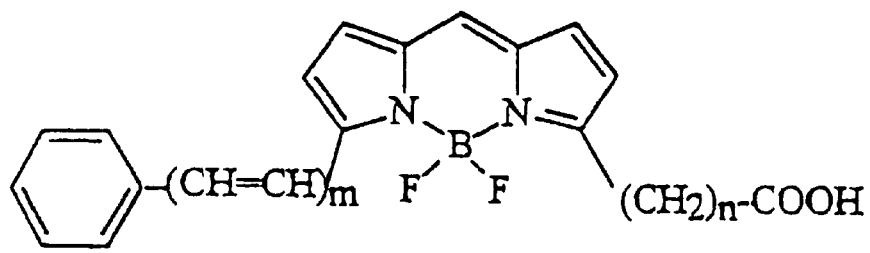
Figure 6B:
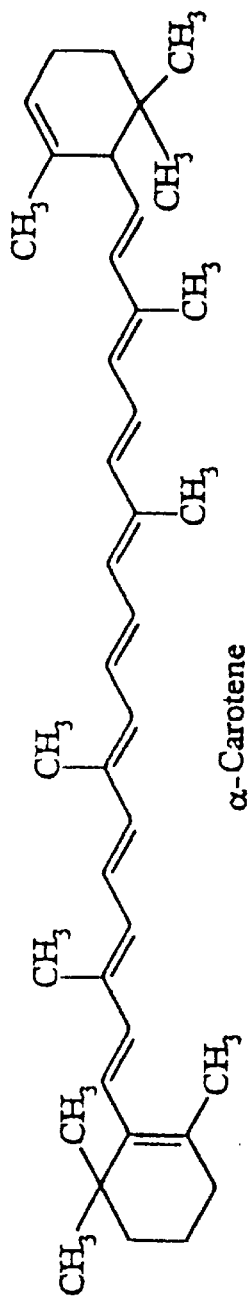
Figure 6B:
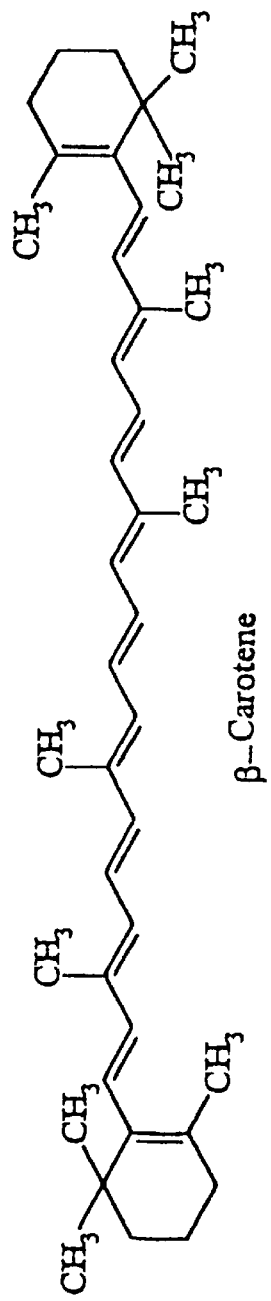
Figure 6B:
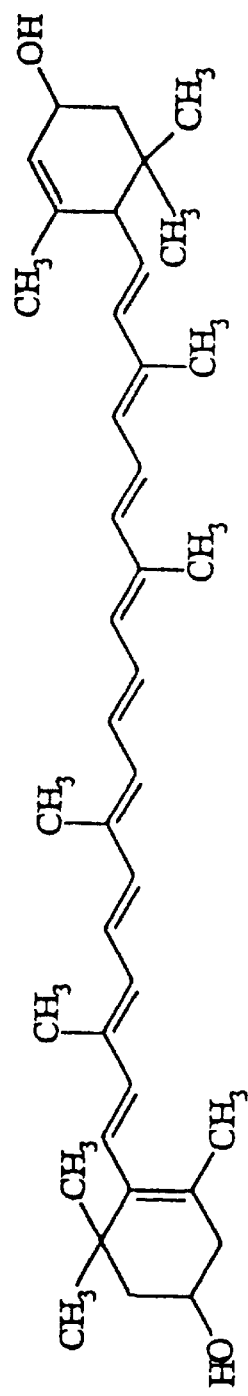
Figure 6C:
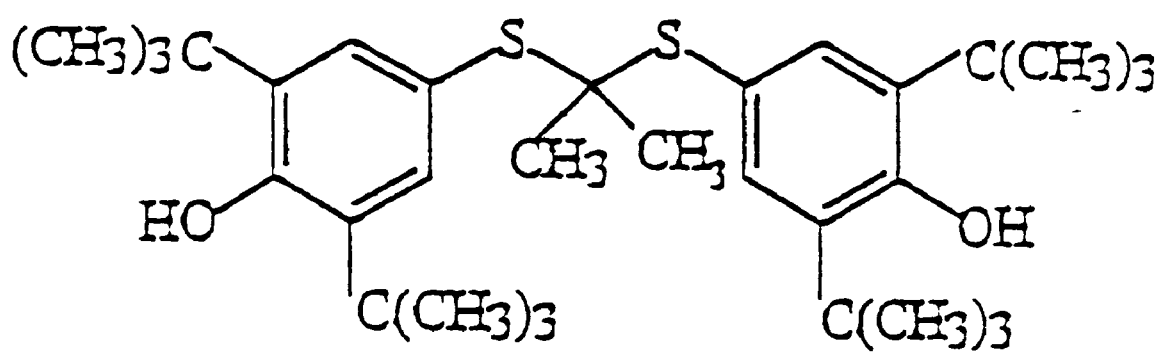

The net antioxidant protection of the fluorescence of BODIPY 581/591 $C_{11}$ in the presence of AMVN provided by the carotenoids α-carotene, β-carotene, and lutein is shown in FIG. 4. The relative peroxyl radical absorbing capacity on a molar basis for Trolox, α-carotene, β-carotene, and lutein was calculated to be 1.00:0.5:0.2:0.7, respectively. Probucol, a lipophylic antioxidant containing a phenolic hydroxyl group, also showed an activity with a molar Trolox equivalence of 0.3, and the kinetic data are shown in FIG. 5. Interestingly, the kinetic decay curve for probucol showed no plateau phase. The commercial source of lutein and α-tocopherol claims they are only 70 and 67% pure, respectively. Assuming the remaining fraction of these samples does not significantly contribute to the total antioxidant activity, then the ratio of the molar Trolox equivalence of Trolox, α-tocopherol, α-carotene, β-carotene, lutein and probucol is calculated to be 1.0:0.9:0.5:0.2:1.0:0.3.

On a per unit weight basis, the relative peroxyl radical absorbing capacity for Trolox, α-tocopherol, α-carotene, β-carotene, lutein and probucol is 1:0.6:0.2:0.1:0.4:0.1, respectively.

We also obtained similar results employing other BODIPY dyes, such as BODIPY 576/589 $C_{11}$, (4,4-difluoro-5-(2-pyrrolyl)-4-bora-3a,4a-diaza-s-indacene-3-propionic acid), and BODIPY 665/676 (E,E)-3,5-bis-(4-phenyl-1,2-cutadienyl)-4,4-difluoro-4-bora-3a,4a-diaza-sindacene acid).

This assay was employed to determine the antioxidant activity of the natural astaxanthin, NatuRose Haematococcus algae. The antioxidiant activity is in agreement with the known amount of astaxanthin, determined spectrophotometrically, and the Trolox equivalence per weight of authentic astaxanthin.

This assay is superior to other assays for a number of reasons. First, it is the first and the only assay which measures the activity of lipophilic antioxidants in a lipid environment employing non-polar fluorophores which absorb in the visible region of the electromagnetic spectrum. Second, it is sensitive, reliable and practicable. Third, it is based on the use of BODIPY dyes, as indicators for peroxyl free radicals, which are characterized by (a) insensitivity to air; (b) thermal and photochemical stability; (c) high fluorescence quantum yields and absorptions with high extinction coefficients; and (d) absorption and fluorescence spectra which are insensitive to solvent polarity and pH.

This assay is suitable for automated microplate fluorometer, and for a flow cytometry technique to examine lipid peroxidation on a cell-by-cell basis.

What is claimed is:

1. A method for measuring antioxidant activity of an antioxidant sample which comprises contacting said sample with a 4,4-difluoro-4-bora-3a,4a diaza-s-indacene (BODIPY) fluorophore, in a medium which comprises a mixture of octane and butyronitrile, and illuminating the resulting solution with an illuminating beam capable of causing said fluorophore to fluoresce, measuring the fluorescence, and comparing the measured fluorescence to a standard.

2. A method according to claim 1, and including the step of measuring fluorescent decay over time.

3. A method according to claim 2, and including the step of heating the sample in the presence of a free radical initiator.

4. A method according to claim 3, and including azabis dimethyl valeronitrile as a free radical initiator.

5. A method according to claim 3, wherein said solvent comprises a non-polar solvent.

6. A method according to claim 3, wherein said fluorophore comprises a BODIPY having unsaturated substituents in conjugation with the parent chromophore.

7. A method according to claim 1, wherein said fluorophore comprises BODIPY 4,4-difluoro-5-(4-phenyl-1,3-butadienyl)-4-bora-3a,4a-diaza-s-indacene-3-undecanoic acid (BODIPY 581/591 $C_{11}$).

8. A method according to claim 1, wherein said fluorophore comprises 4,4-difluoro-3,5-bis(4-phenyl-1,3-butadienyl)-4-bora-3a,4a-diaza-s-indacene (BODIPY 665/676).

9. A method according to claim 1, wherein said fluorophore comprises 4,4-difluoro-5-(2-pyrrolyl)-4-3a,4a-diaza-s-indacene-3-undecanoic acid (BODIPY 576/589 $C_{11}$).

10. A method according to claim 1, wherein said medium comprises 90% octane and 10% butyronitrile, by volume.

11. A method for measuring antioxidant activity of a sample suspected of having such activity, which method comprises the steps in sequence of:

(a) initiating a free radical induced oxidation reaction, in a lipophilic phase which comprises a mixture of octane and butyronitrol, of a BODIPY fluorophore having unsaturated substituent(s) in conjugation with the parent chromophore (4,4-difluoro-4-bora-3a,4a-diaza-s-indacene);

(b) illuminating the reaction mixture from step (a) with an illuminating beam capable of causing said fluorophore to fluoresce, and measuring fluorescence;

(c) monitoring the disappearance of fluorescence while allowing said reaction to progress thereby to cause gradual loss of fluorescence over a period of time;

(d) contacting said sample with said free radical induced oxidation reaction product of BODIPY fluorophore;

(e) monitoring any change in the protection of the fluorescence signal of said BODIPY fluorophore; and (f) determining the antioxidant activity of said sample by comparing the fluorescence signal of said sample to the fluorescence signal a sample of known antioxidant activity subjected to steps (a) to (e).

12. A method according to claim 11, wherein said fluorophore comprises a BODIPY structure with conjugated unsaturated substituent(s) capable of reaction with free radicals.

13. A method of claim 12, wherein said BODIPY comprises 4,4-difluoro-5-(4-phenyl-1,3-butadienyl)-4-bora-3a,4a-diaza-s-indacene-3-undecanoic acid (BODIPY 581/591 $C_{11}$).

14. A method of claim 12, wherein said BODIPY comprises 4,4-difluoro-3,5-bis(4-phenyl-1,3-butadienyl)-4-bora-3a,4a-diaza-s-indacene (BODIPY 665/676).

15. A method of claim 12, wherein said BODIPY comprises 4,4-difluoro-5-(2-pyrrolyl)-4-bora-3a,4a-diaza-s-indacene-3 undecanoic acid (BODIPY 576/589 $C_{11}$).

16. A method according to claim 11, wherein said free radical is generated by heating a free radical initiator.

17. A method of claim 16, wherein said free radical initiator comprises azo-bis-dimethyl valeronitrile.

18. A method of claim 11, wherein said lipophilic phase comprises 90% octane and 10% butyronitrile, by volume.

* * * * *